US006699281B2

(12) United States Patent
Vallana et al.

(10) Patent No.: US 6,699,281 B2
(45) Date of Patent: Mar. 2, 2004

(54) ANGIOPLASTY STENTS (75) Inventors: Franco Vallana, Turin (IT); Giovanni Rolando, Chivasso (IT); Maria Curcio, Saluggia (IT); Paolo Gaschino, Chivasso (IT)

(73) Assignee: Sorin Biomedica Cardio S.p.A., Saluggia (IT)

( * ) Notice: Subject to any disclaimer, the term of this patent is extended or adjusted under 35 U.S.C. 154(b) by 0 days.

(21) Appl. No.: 10/198,054

(22) Filed: Jul. 18, 2002

(65) Prior Publication Data

US 2003/0028242 A1 Feb. 6, 2003

(30) Foreign Application Priority Data

Jul. 20, 2001 (EP) .............................. 01830489

(51) Int. Cl.$^7$ ................................. A61F 2/06
(52) U.S. Cl. .................................... 623/1.42
(58) Field of Search ................... 623/1.15, 1.42–1.48

(56) References Cited

U.S. PATENT DOCUMENTS

| | | | |
|---|---|---|---|
| 5,084,151 A | | 1/1992 | Vallana et al. |
| 5,133,845 A | | 7/1992 | Vallana et al. |
| 5,370,684 A | | 12/1994 | Vallana et al. |
| 5,387,247 A | | 2/1995 | Vallana et al. |
| 5,423,886 A | | 6/1995 | Arru et al. |
| 5,609,629 A | | 3/1997 | Fearnot et al. |
| 5,733,303 A | * | 3/1998 | Israel et al. ............... 623/1.15 |
| 5,824,049 A | | 10/1998 | Ragheb et al. |
| 6,071,305 A | * | 6/2000 | Brown et al. ............. 623/1.43 |
| 6,096,070 A | | 8/2000 | Ragheb et al. |
| 6,120,847 A | * | 9/2000 | Yang et al. ................. 427/335 |
| 6,193,747 B1 | * | 2/2001 | von Oepen ................ 623/1.15 |
| 6,254,632 B1 | | 7/2001 | Wu et al. |
| 6,273,913 B1 | * | 8/2001 | Wright et al. ............. 623/1.42 |
| 6,299,604 B1 | | 10/2001 | Ragheb et al. |
| 6,315,794 B1 | * | 11/2001 | Richter ..................... 623/1.34 |
| 6,379,381 B1 | * | 4/2002 | Hossainy et al. .......... 623/1.42 |
| 6,387,121 B1 | * | 5/2002 | Alt ............................ 623/1.15 |
| 6,398,806 B1 | * | 6/2002 | You .......................... 623/1.15 |
| 6,451,049 B2 | * | 9/2002 | Vallana et al. ............. 623/1.15 |
| 6,506,437 B1 | * | 1/2003 | Harish et al. .............. 427/2.25 |
| 6,551,353 B1 | * | 4/2003 | Baker et al. ............... 623/1.42 |
| 6,562,065 B1 | * | 5/2003 | Shanley .................... 623/1.15 |
| 6,569,195 B2 | * | 5/2003 | Yang et al. ................ 623/1.46 |
| 6,585,764 B2 | * | 7/2003 | Wright et al. ............. 623/1.42 |

FOREIGN PATENT DOCUMENTS

| | | |
|---|---|---|
| EP | 0 747 069 A2 | 12/1996 |
| EP | 0 806 190 A1 | 11/1997 |
| EP | 0 850 604 A2 | 7/1998 |
| EP | 0 857 470 A2 | 8/1998 |
| EP | 0 875 215 A1 | 11/1998 |
| EP | 0 895 759 A1 | 2/1999 |
| EP | 0 895 760 A1 | 2/1999 |
| EP | 0 950 386 A2 | 10/1999 |
| EP | 1 080 738 A1 | 3/2001 |
| EP | 1 088 528 A1 | 4/2001 |
| EP | 1 103 234 A1 | 5/2001 |
| WO | WO 98/23228 | 6/1998 |
| WO | WO 01/17577 A1 | 3/2001 |

OTHER PUBLICATIONS

European Search Report for corresponding application 01830489.9 (2 pages) Co–pending, commonly assigned U.S. Ser. No. 08/997,597.

* cited by examiner

*Primary Examiner*—David H. Willse
*Assistant Examiner*—Suzette J. Jackson
(74) *Attorney, Agent, or Firm*—Popovich, Wiles & O'Connell, P.A.

(57) ABSTRACT

A stent for use at an implant site in a vessel having recesses containing one or more active agents. The stent is a tubular body having a plurality of sinusoidal shaped annular elements and connection elements. The recesses are formed so as to leave substantially unaltered the bending moments of these elements. The recesses may be continuous or discontinuous and may be distributed uniformly or nonuniformly.

6 Claims, 6 Drawing Sheets

ANGIOPLASTY STENTS

FIELD OF THE INVENTION

The present invention relates to stents, and in particular, relates to angioplasty stents adapted to convey therapeutic agents.

BACKGROUND OF THE INVENTION

The term "stent" is intended to indicate devices intended for endoluminal application (e.g. within a blood vessel), normally fitted via catheterization, with subsequent deployment in situ so as to provide a local supporting effect for the lumen. Stents are extensively disclosed in the patent literature, for example co-pending, commonly assigned EP 0 806 190, EP 0 850 604, EP 0 857 470, EP 0 875 215, EP 0 895 759, EP 0 895 760, EP 1 080 738, EP 1 088 528, and EP 1 103 234.

In particular, the present invention falls within the line of research aimed at developing solutions that enable the stent to be used as a vehicle for delivery of active or activatable agents of various nature (e.g., pharmacological agents, radioactive agents, etc.) designed, for example, to inhibit restenosis. Solutions of this sort are described, in the framework of the documents cited above, in EP 0 850 604, EP 1 080 738, and EP 1 103 234.

In particular, EP 0 850 604 describes the possibility of providing, on the surface of a stent, in particular on its outer surface, a sculpturing having the function of increasing the surface area of the stent in such a way as to create undercuts and/or, in general, a surface roughness in order to facilitate application of coatings of active or activatable agents. The sculpturing, consisting for instance of microspheres, may also increase adhesion of the stent to the wall of the vessel being treated.

The most recent clinical developments have revealed that limiting the intervention to coating the surface of the stent with active or activatable agents may encounter various difficulties and/or problems.

First, the amount of agent with which the stent is coated may in actual fact prove insufficient, particularly when the aim is to obtain a release, and hence an action, that is prolonged in time. Further, in applications of vascular angioplasty, the surfaces of the stent, and in particular the inner surface, are subjected to an action of flushing by the blood flow.

Second, for the reason just mentioned, it is desirable that the active or activatable agent should be carried and released prevalently, if not exclusively, on the outer surface of the stent, and not on its inner surface. This is particularly true in the case where the agent applied on the stent is designed to perform an antagonistic function in regard to restenosis. In these situations, the function of the active agent, which is aimed at acting on the outer surface of the stent facing the wall of the vessel undergoing treatment may have unfavorable effects in areas corresponding to the inner surface; for example, the phenomena of neointima formation on the inner surface of the stent, which are considered to be beneficial in the phases subsequent to the implant phase, may be hindered.

In the above general framework, it would be desirable to have available stents that include reservoirs of active or activatable agents, possibly different from one another, available in sufficient quantities to achieve a beneficial effect that may be prolonged over time. Further, it would be desirable to have stents capable of carrying available agents that are different from one another, located selectively in different positions along the stent, with the additional possibility of selectively varying the dosages in a localized way, for instance achieving dosages that are differentiated in the various regions of the stent.

On the other hand, it should not be forgotten that a stent is always configured as a structural element, in the sense that, once placed in the implantation site and brought into its radially expanded condition, the stent must be able to maintain the perviousness of the treated vessel without being subject to appreciable phenomena of contraction or collapse resulting from the radial compressive loads applied on the stent by the walls of the treated vessel.

This explains why the known solutions, aimed at creating on the surface of the stent irregularities such as might contain or enable anchorage of coatings and/or agents of various nature, have so far involved only quite a contained portion of the cross section of the parts (radially expandable annular elements, longitudinal elements of connection) of which the stent is normally composed.

SUMMARY OF THE INVENTION

The purpose of the present invention is to make a stent of an improved type which is able to reconcile in an optimal way the characteristics of longitudinal flexibility, which are required, for example, during the phase in which the stent is made to advance towards the implantation site, with the characteristics of plastic behavior required for the stent to be able to perform an altogether effective action of support after being expanded or dilated, minimizing and virtually eliminating any phenomena of recoil.

The object of the present invention is thus to provide a solution that is able to overcome in a decisive way the difficulties and drawbacks referred to above.

It will be appreciated that in the present description and in the annexed claims the term "stent" is used in its broadest sense, referring in general terms to any device having an overall tubular shape which is able to support the lumen of a segment of a blood vessel or any other anatomic lumen to prevent blockage of fluid flow. It therefore follows that the scope of the invention must not in any way be understood as being limited to stents for vascular angioplasty. The range of possible application of the invention extends, for example, to stents for treating aneurysms and/or to so-called "stent-grafts".

In one aspect, this invention is a stent for use at an implant site in a vessel comprising a radially expandable tubular body and an active agent for treatment of the implant site, the tubular body having an interior surface and an exterior surface, the tubular body including a plurality of sinusoidal shaped annular elements and a plurality of lambda shaped connection elements, each annular element being connected to at least one other annular element by a plurality of connection elements, each annular element and each connection element having a rectilinear portion and a curved portion, the exterior surface of the tubular body having a plurality of recesses positioned only in the rectilinear portions, the active agent being contained within the recesses, the recesses conferring on the rectilinear portion where they are positioned a hollowed sectional profile of which the recesses occupy from 10% to 60% of the area of the sectional profile, the geometry of the recesses being such that bending moments of inertia of the portions containing the recesses are not substantially reduced. The hollowed sectional profile of the recesses may also range from 20% to 50% of the area of the sectional profile, or may be not less than 30% of the area of the sectional profile. The hollowed sectional profile of the recesses may have undercut areas, a C-shaped profile, a U-shaped profile, a V-shaped profile, or a rectangular profile. The stent also has a longitudinal axis and the longer dimension of the rectangular profile may extends in a direction tangential to or radial to the longitudinal axis. The plurality of recesses may be substantially continuous or discontinuous on the exterior surface of the rectilinear portions of the stent, and each recess may have a substantially well-shaped configuration. The exterior surface of the stent may have a coating of biocompatible carbon material. The plurality of recesses may have a coating of biocompatible carbon material. The active agent may comprise at least two different active agents, and may be present in a non-uniform distribution along the longitudinal axis of the stent.

In a second aspect, this invention is a stent for use at an implant site in a vessel comprising a radially expandable tubular body and an active agent for treatment of the implant site, the tubular body having an interior surface and an exterior surface, the tubular body including a plurality of annular elements and a plurality of connection elements, each annular element being connected to at least one other annular element by at least two connection elements, the tubular body having a plurality of recesses, the active agent being contained within the recesses, the recesses conferring on the elements where they are positioned a hollowed sectional profile of which the recesses occupy a portion of the area of the sectional profile, the geometry of the recesses being such that bending moments of inertia of the elements containing the recesses are not substantially reduced. In a preferred embodiment, the plurality of recesses are on the exterior surface of the stent. The hollowed sectional profile of the recesses may range from 10% to 60% of the area of the sectional profile.

In a third aspect, this invention is a stent for use at an implant site in a vessel comprising a radially expandable tubular body and an active agent for treatment of the implant site, the tubular body having an interior surface and an exterior surface, the tubular body including a plurality of annular elements and a plurality of connection elements, the annular elements and connection elements having portions subject to stress during expansion or use of the stent and portions not subject to stress during expansion or use of the stent, each annular element being connected to at least one other annular element by a plurality of connection elements, the tubular body having a plurality of recesses positioned only in the portions that are not subject to stress during expansion or use of the stent, the active agent being contained within the recesses, the recesses conferring on the portions where they are positioned a hollowed sectional profile of which the recesses occupy a substantial portion of the area of the sectional profile, the geometry of the recesses being such that the characteristic of bending strength of the portions containing the recesses is not substantially reduced. In a preferred embodiment, the hollowed sectional profile of the recesses is not less than 30% of the area of the sectional profile.

In a fourth aspect, this invention is a stent for use at an implant site in a vessel comprising a radially expandable tubular body and an active agent for treatment of the implant site, the tubular body having an interior surface and an exterior surface, the tubular body including a plurality of annular elements and a plurality of connection elements, the annular elements and connection elements having portions subject to deformation during expansion or use of the stent and portions not subject to deformation during expansion or use of the stent, each annular element being connected to at least one other annular element by a plurality of connection elements, the tubular body having a plurality of recesses positioned only in the portions that are not subject to deformation during expansion or use of the stent, the active agent being contained within the recesses, the recesses conferring on the portions where they are positioned a hollowed sectional profile of which the recesses occupy a substantial portion of the area of the sectional profile, the geometry of the recesses being such that the characteristic of bending strength of the portions containing the recesses is not substantially reduced.

BRIEF DESCRIPTION OF THE DRAWINGS

The invention will now be described, purely by way of a non-limiting example, with reference to the annexed drawings, in which.

DETAILED DESCRIPTION OF THE PREFERRED EMBODIMENTS

The solution according to the invention is suitable for being applied to particular advantage in stents designed to be provided, at least on part of their surfaces, with a coating of biocompatible carbon material of the type described, for instance, in U.S. Pat. Nos. 5,084,151 (Vallana et al.), 5,133,845 (Vallana et al.), 5,370,684 (Vallana et al.), 5,387,247 (Vallana et al.), and 5,423,886 (Aru et al.).

Figure 1:
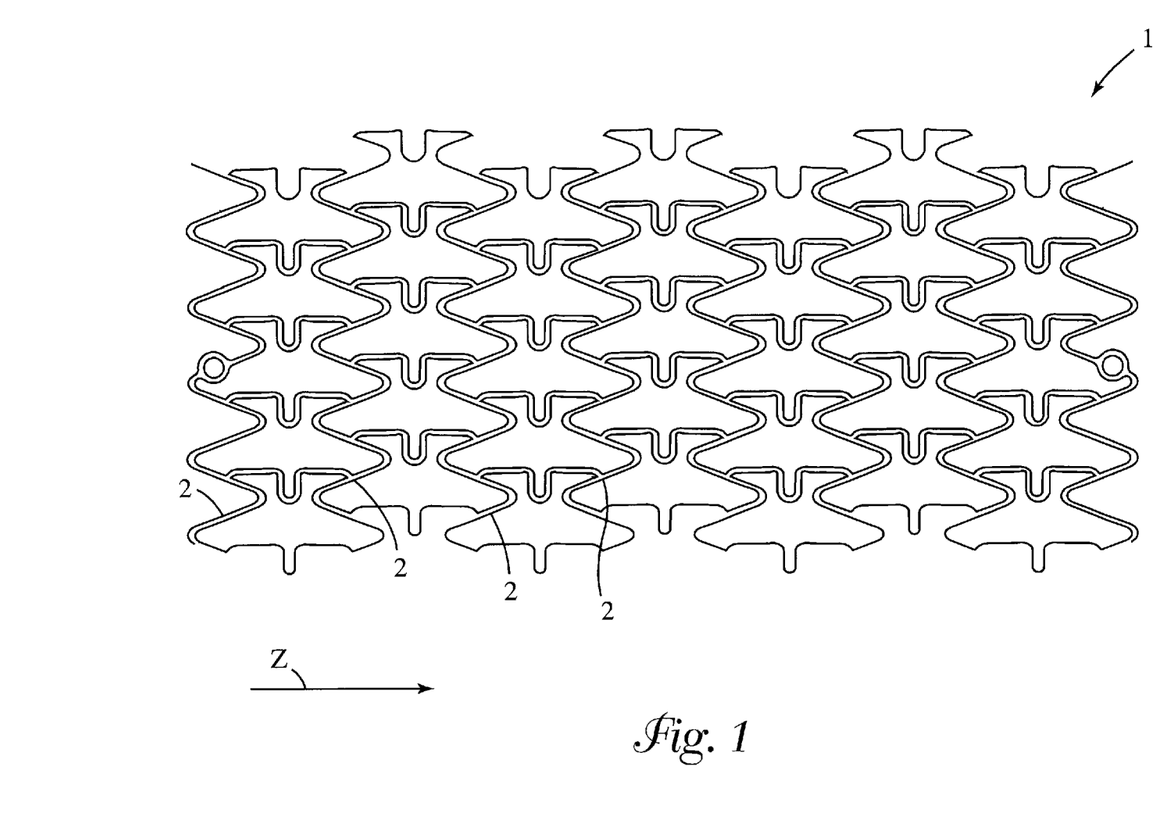
FIG. 1 is a plan view of the tubular stent of the present invention cut longitudinally and opened to lie within a single plane, the stent being in a radially contracted configuration.

FIG. 1 shows a stent, which generally comprises a plurality of annular elements 2 having a roughly cylindrical shape and a serpentine pattern, which are designed to be aligned in sequence along the main axis of the stent designated as the Z axis. The above may be, for instance, a stent of the type illustrated in the document EP 0875215.

In FIGS. 1 to 4, the reference number 1 designates part of the structure of any known type of stent, comprising a radially expandable tubular body made up of elements defining a reticular structure. Elements that vary from one embodiment to another but otherwise are similar in function are denoted by suffices "a", "b", "c", etc., and may be referred to in a general way by a number without its suffix.

The various annular elements 2 are connected together by means of longitudinal connection elements 3, generally referred to as "links" and have, in the example of embodiment herein illustrated, a general lambda configuration. Preferably, and according to a configuration in itself known, the connection elements 3 are connected to the cylindrical elements 2 at the "0" points of the respective sinusoidal paths. The elements 2 and 3 described above thus constitute respective branches of the reticular structure of the stent 1.

The geometrical particulars of the stent 1 do not, however, constitute a limiting or binding element of the invention; the solution according to the invention can, in fact, be applied to stents of any type, shape or dimensions. Even though the invention has been developed with particular attention paid to the possible use in the sector of stents obtained starting from a microtube, the solution according to the invention can also be applied to stents obtained, for instance, starting from variously shaped filiform materials (the so-called "wire" stents).

The solution according to the invention is based upon the realization that the characteristics of structural strength of the parts constituting the stent (in the example of embodiment herein illustrated, the annular elements 2 and the links 3) are not generally impaired even when the cross section of those parts is—even markedly—hollowed out, provided that the formation of the corresponding hollow parts or recesses is such as not to jeopardize the characteristics of flexural strength of the parts, the characteristics being identified in particular by the corresponding bending moments of inertia.

Figure 2:
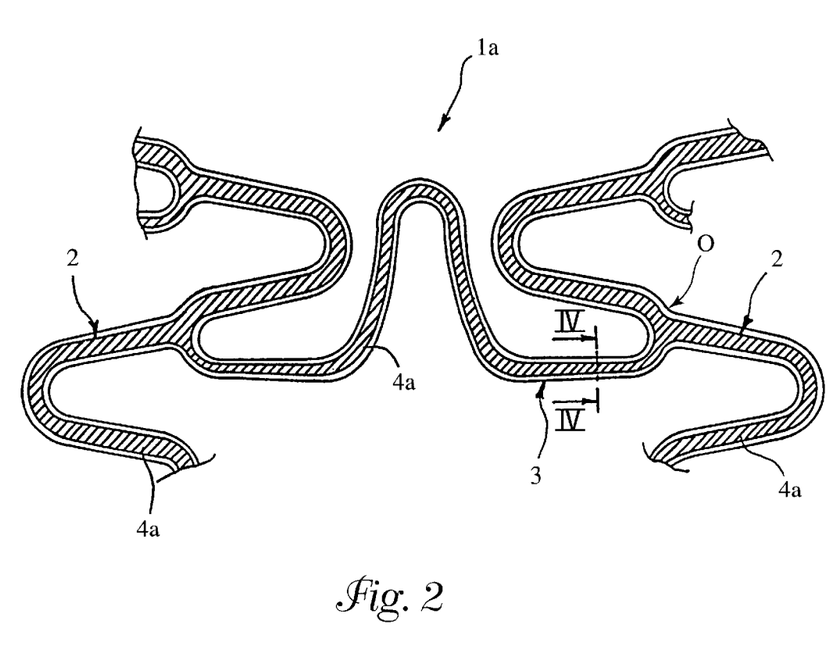
FIGS. 2 to 4 illustrate partial plan views of three embodiments of the stent of this invention.
Figure 3:
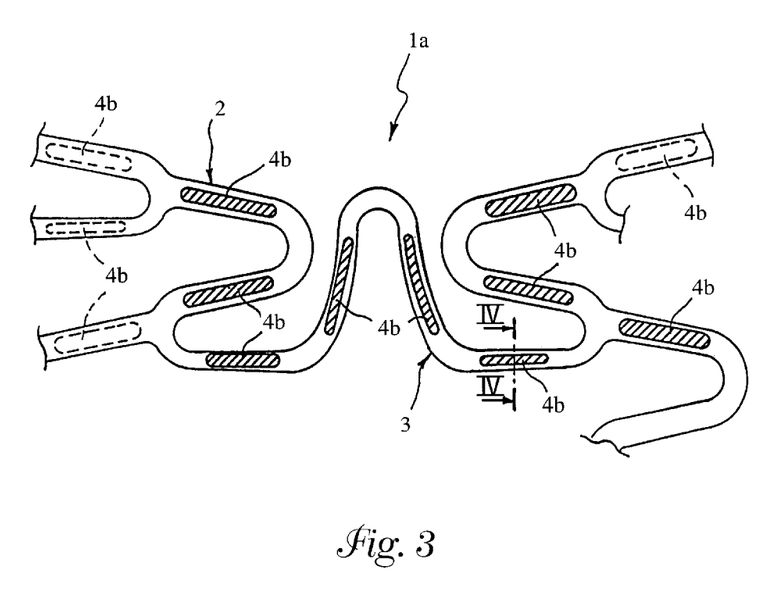
Figure 4:
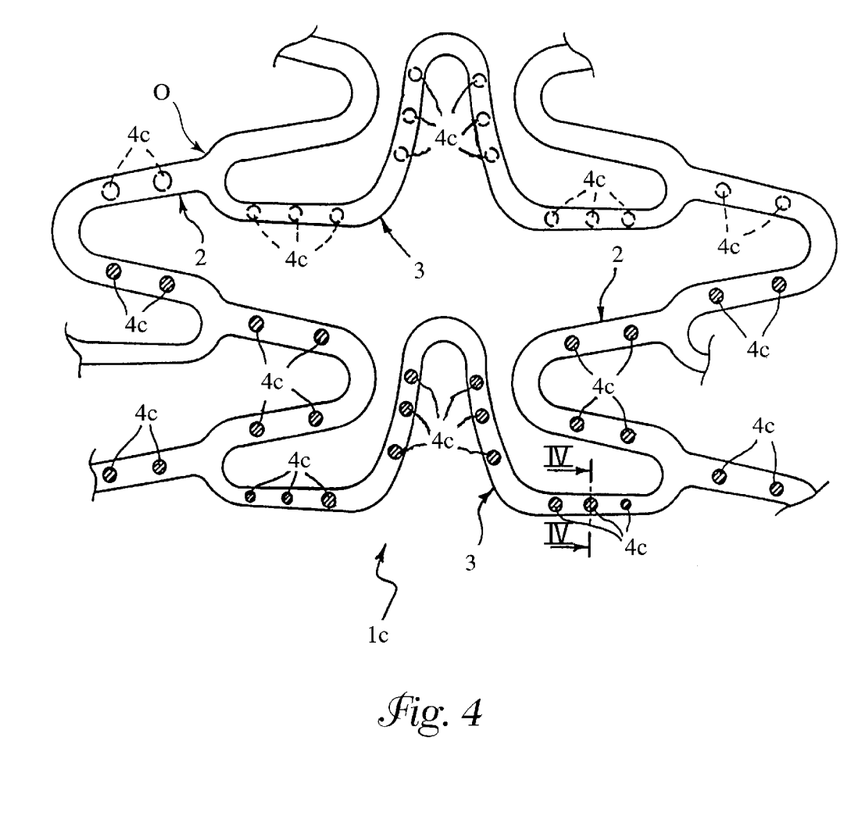
Figure 5:
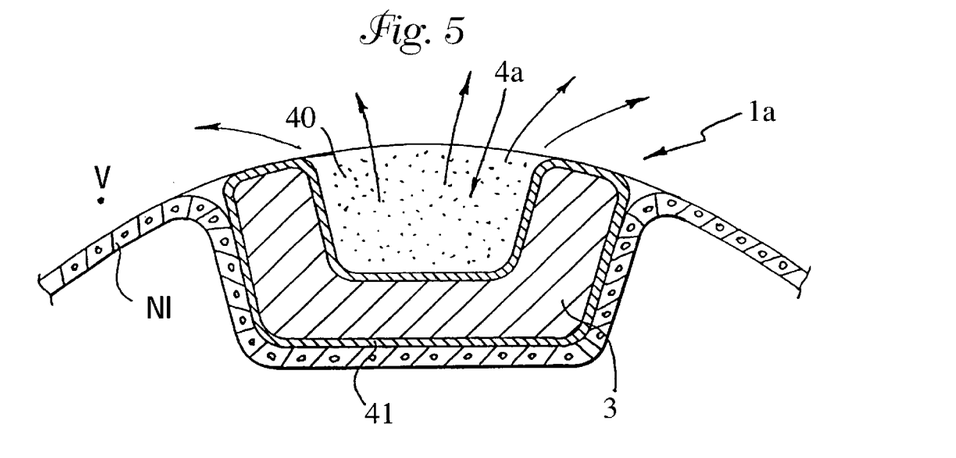
FIG. 5 is an enlarged cross sectional view of a stent according to FIG. 1, 2, 3 or 4.

FIGS. 2 to 4 illustrate three embodiments of the invention. In all three cases it is envisioned that the elements 2 and 3 of the stent, which have in general a filiform or bar-like configuration (or, resorting to a more appropriate term drawn from structural mechanics, a "beam" configuration) are subjected to an action of reduction of their section, obtaining in the parts themselves, and preferably on the surfaces facing the outside of the stent 1, recesses, designated as a whole by 4, as best seen in FIG. 5. Recesses 4 are able to receive respective fillings 40 of active or activatable agents of various nature (for example, pharmacological agents, radio-active agents, etc.) designed, for instance, to perform a restenosis-antagonist function.

In the embodiment illustrated in FIG. 2, the recesses amount to a single recess 4a which extends practically without any discontinuities over the entire outer surface of stent 1a.

The embodiment shown in FIG. 3 illustrates that the recesses 4b of stent 1b are chiefly, if not exclusively, made in areas corresponding to the rectilinear or substantially rectilinear portions of the parts 2 and 3, avoiding in particular both the curved parts (for example, the cusp parts of the sinusoidal path of the elements 2, the cusp part of the central loop of the links 3, and the areas of connection of the central loop to the side branches of the links 2 themselves) and the areas in which the links 3 are connected to the elements 2.

The above-mentioned cusp and/or connection parts correspond to the areas that are to undergo deformation during normal operation of the stent, and in particular during expansion of the stent from the radially contracted implant condition to the radially expanded condition in which the stent supports the vessel. In other words, in the embodiment of FIG. 3, the formation of recesses 4b is limited just to the areas of the elements 2 and 3 that will be less subject to stress during operation of the stent. The embodiment of FIG. 4 relates, instead, to the possibility of making the recesses 4c in the form of separate wells set at a distance apart from one another and variously distributed over the surface of the stent 1c.

As may be clearly seen, the representation of FIGS. 2 to 4 highlights characteristics of implementation that may also be used in combination with one another. For example, according to the specific requirements of application and treatment, it is possible to envision that in certain parts of the stent the solution represented in FIG. 2 will be adopted, resorting, instead, in other areas of the stent to solutions of the type represented in FIGS. 3 and 4. All three solutions represented in the figures may therefore be freely combined with one another even in a single stent.

The solutions represented in FIGS. 3 and 4, in which the recesses 4b and 4c, respectively, consist of hollowed-out formations separate from one another prove particularly advantageous in those applications in which recesses 4 are designed to function as reservoirs to enable arrangement of active/activatable agents of a different nature on the stent 1.

For example, with reference for reasons of simplicity to the solution illustrated in FIG. 4, where this possibility is more evident, each recess 4c could receive within it an active/activatable agent having different characteristics. At least in principle, this solution makes it possible to have available on the stent, virtually and in principle, as many different agents as there are recesses 4.

More commonly the recesses 4 of the solution illustrated in FIG. 4 can be used to put different agents in different areas of the stent 1. For instance, the recesses located at the ends of the stent can receive anti-inflammatory agents since the end parts of the stent are the ones most exposed to the possible onset of inflammatory phenomena.

In any case, it is emphasized that the present invention relates primarily to the structure of the stent 1 and does not specifically regard the nature, characteristics, and dosages of the agents—which may be of any nature—that are to be accommodated in the recesses 4.

An important characteristic of the solution according to the invention is provided by the possibility, better illustrated in the cross-sectional view of FIG. 5 (and in the views of FIGS. 6 to 9, which constitute respective variants), of obtaining the recesses 4 not only in the form of a surface sculpturing, but also in the form of cavities which occupy a substantial part of the cross-sectional area of the stent/part/element (in the example of FIG. 5, this is one of the links 3) in which the recess 4 is made.

For instance, recess 4 illustrated in FIG. 5 occupies a portion corresponding to approximately 30% of the overall section (more precisely, of the overall sectional area) of the surface of envelope of the cross section of the element considered. The aforesaid percentage value is typically within the 10% to 60% range, preferably in the 20% to 50% range, and, even more preferably not less than 30%.

It will on the other hand be appreciated that the values and ranges of values herein indicated may be extended or modified without prejudice to the affects pursued, as will be evident from the present description to a person skilled in the art.

In the embodiment illustrated in FIG. 5, the above-mentioned recess 4 has an approximately rectangular profile, so that the "full" part of the element 3 in which the recess 4 is made has a generally C-shaped pattern. An overall C-shaped pattern may be encountered also in the elements 3 illustrated in the variants of FIGS. 6 to 9. The aim here has been to highlight the fact that the recess 4 (which in the figure has an approximately rectangular shape, with the main dimension in the direction of the width of the element 3, i.e., in a direction that is tangential to stent 1c may have profiles of a different type.

Figure 6:
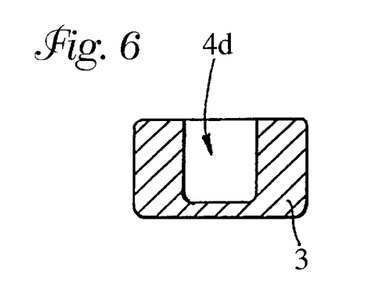
FIGS. 6 to 9 each illustrate an alternate cross sectional configuration for the stent of this invention.
Figure 7:
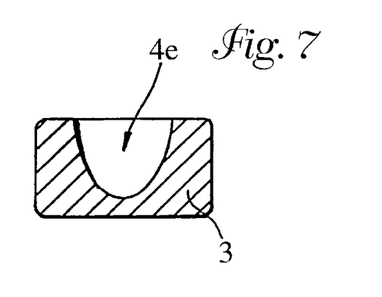
Figure 8:
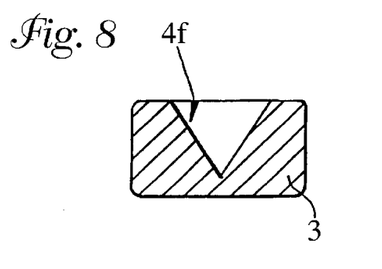

For example, this may be, as in the case of FIG. 6, a recess 4d with a rectangular cross-sectional profile, but with the larger dimension in the direction of the depth of the element 3, i.e., in the radial direction of the stent 1. Alternatively, it may be an overall U-shaped profile (4e in FIG. 7), or else a V-shaped profile (4f in FIG. 8), or yet again a profile such as to bestow on the element 3 a general channel-shaped pattern with an inlet part of the recess 4 that has dimensions smaller than the maximum dimensions of the recess 4 itself, according to a general "undercut" configuration (4g in FIG. 9). Of course, it is also possible to make the recesses 4 in such a way that, instead of being blind as in the case of the embodiments illustrated herein, they at least marginally pass through the body of the element 3.

Tests carried out by the present applicant have shown that, if known techniques are used (such as chemical etching, the use of physical etching agents, for example laser-beam or ion-beam etching), it is possible to make, in the elements 3, recesses 4 the sectional area of which ranges from 10% to 60% of the overall sectional area of the envelope of the element considered, without detriment to the characteristics of structural strength, and hence functionality, of the elements 2 and 3, provided that the recess 4 is obtained according to modalities that do not produce an appreciable reduction in the bending moments of inertia (measured both in the radial direction and in the tangential direction with respect to the development of the stent) of the elements 2 and 3.

Of course, the aforesaid effect of reduction of the section and conservation of the moments of inertia is with reference to the cross section (see the cross-sectional line IV—IV of FIGS. 2 to 4) measured in the area in which the recess 4 is located.

In particular, in the case of the embodiment of FIG. 2, the recess 4a of stent 1a is present practically throughout the development of the stent, so that the condition referred to above must be encountered practically throughout the structure of the stent.

In the embodiment of FIG. 3, the aforesaid condition is to be respected in the areas of extension of the recesses 4, this condition being, on the other hand, automatically met in the rounded end areas of the recesses 4 themselves.

Finally, in the case of the well-shaped recesses 4 represented in FIG. 4, the aforesaid condition must be satisfied in the maximum diametral plane of the recess. Also in this case, once this condition has been met in the aforesaid maximum sectional plane, it is automatically satisfied also in the other sectional planes.

What has been said in regard to the well-shaped recesses of FIG. 4 of course also applies to recesses (not specifically illustrated in the drawing, but comprised in the scope of the present invention) which envision areas of variable cross section throughout the longitudinal development of the recess.

From an observation of the cross-sectional view of FIG. 5 it is possible to realize that the presence of recesses, preferably made on the outer surface of the stent, enables arrangement of a wide reservoir for gathering active/activatable agents that can be released from the stent to the adjacent tissue.

Since the recesses 4 are made preferably in the outer surface of the stent, the phenomenon of release may take place preferably in a centrifugal direction, i.e., from the outside of the stent 1 towards the wall of the vessel V undergoing treatment, thus containing to a very marked extent the phenomena of possible diffusion in a radial direction towards the inside of the stent 1. In this way it is possible to prevent undesired antagonistic phenomena in regard to the possible neointima formation, such as the neointima structure indicated by NI in FIG. 5.

Figure 9:
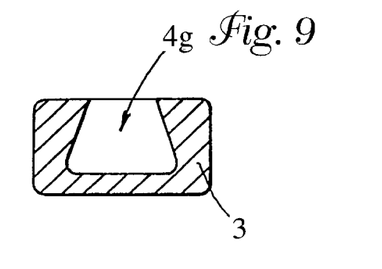

Having available recesses 4 of relatively large dimensions (and not ones limited to a modest surface roughness of the stent) renders less critical the aspect of the physical anchorage of the agent or agents to the surface of the stent. It may indeed be stated that the solution according to the invention makes it possible to pass from a logic of pure and simple "coating" of the stent to an approach that uses stent 1 itself as a true container/supplier of active/activatable agents. The effect of containment is more marked in the case where, as illustrated in FIG. 9, the recess 4g can be made in undercut conditions, hence with an effect of mechanical retention of therapeutic agents within the recess.

Figure 10A:
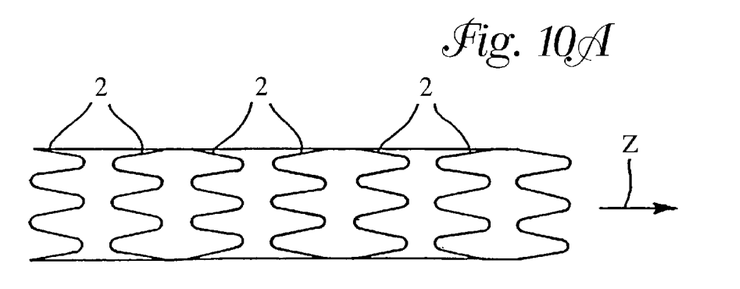
FIG. 10A is a partial schematic view of a stent of this invention and FIGS. 10B to 10D are graphical representations of the distribution of therapeutic agents in the longitudinal length of the stent.

FIG. 10A is a partial schematic view of a tent of this invention, in which a plurality of annular elements 2 having a roughly cylindrical shape and a serpentine pattern are designed to be aligned in sequence along the main axis of the stent designated as the Z axis.

Figure 10B:
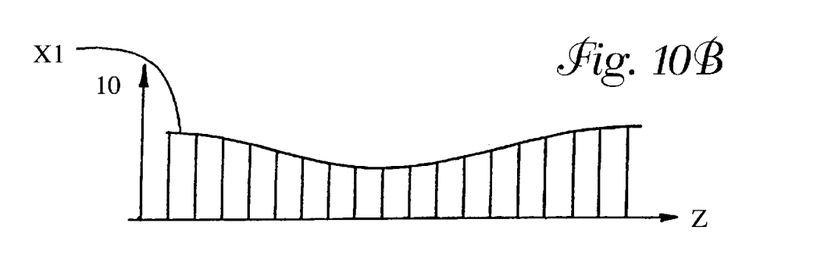
Figure 10C:
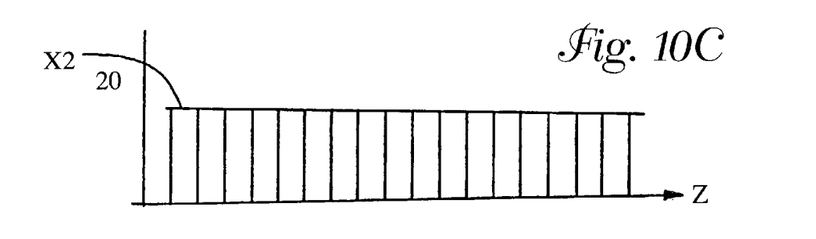
Figure 10D:
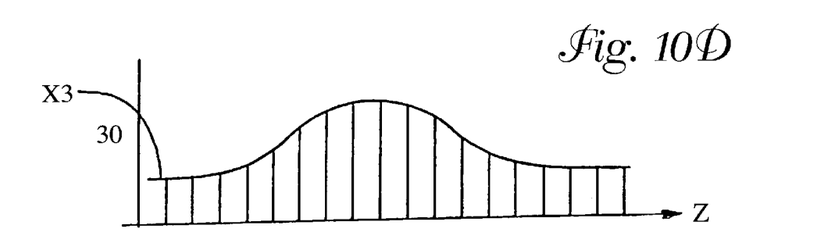

The graphs of FIGS. 10B, 10C and 10D illustrate how different agents 10, 20, and 30 may be distributed longitudinally along the stent. For example, the location of therapeutic agents can exploit the spatial distribution of the well-shaped recesses illustrated in FIG. 4. Also, the types and/or concentrations of agents can be varied so as to present levels of concentration X1, X2, X3 differentiated along the longitudinal development of the stent.

In particular, the diagram of FIG. 10B illustrates the possible use of a first agent 10 (for example, an anti-inflammatory agent) with a higher concentration at the ends of the stent as compared to the central area of the stent. FIG. 10C illustrates the use of agent 20 (for example, an anti-mitotic agent) with a level of concentration X2 that is constant throughout the longitudinal development of the stent. In FIG. 10D, another agent 30 (for example, a cytotoxic agent) with a maximum level of concentration X3 in the central area of the stent and decreasing levels toward the ends of the stent.

In addition, FIG. 5 illustrates that, according to a particularly preferred embodiment of the invention, the entire surface of stent 1 (with the possible exclusion of the surface of the recess 4a, even though this fact is not of particularly determining importance) may be coated with a layer of biocompatible carbon material 41 having the characteristics, and applied according to the modalities, described in the various U.S. Patents cited above.

A coating of carbon material performs an anti-thrombogenic function, favoring endothelization and—a factor that is deemed of particular importance—acting in the direction of preventing release of metal ions from the stent 1 to the surrounding tissue.

As regards the technologies of implementation, the recesses 4 may be made, as has already been said, starting from a pre-existing stent structure, and then obtaining (using chemical, physical and/or mechanical means) an action of removal of material aimed at producing the formation of the recesses 4.

In an embodiment that has proved particularly advantageous, relating to stents obtained starting from a microtube, the recesses 4 are made in the microtube before cutting of the stent is carried out.

Of course different embodiments are possible. For example, in the case of wire stents, a sectional profile of the type illustrated in FIGS. 5 to 9 can be obtained by drawing when the wire is being made.

As regards the choice of the sectional profile which is determined by the formation of the recesses 4, the general C-shaped profile of the element 3 represented in FIGS. 5 to 9, whilst constituting a preferred choice, is not an imperative choice. For example, it is possible to adopt profiles of different section, for example an H-shaped section, an L-shaped section, or a T-shaped section. The C-shape is preferred in so far as it enables the recess 4 to be obtained in such a way that it emerges directly and exclusively on the outer surface of the stent.

As regards the definition of the dimensions of the recesses 4, it is to be recalled that the percentage values indicated herein refer in general to the ratio between the sectional area corresponding to the recess 4 and the overall sectional area of the envelope of the element of the stent in which the recess is made, including also the sectional area of the recess.

As compared to traditional embodiments, hence ones with elements 2, 3 having a full section (i.e., without recesses such as the recesses 4), the elements of a stent made according to the present invention may present a sectional area that is possibly oversized with respect to the homologous sectional areas of the "full" elements of traditional stents.

In this connection, a number of examples of possible application of the solution according to the invention follow.

EXAMPLE 1

Reference is made to an element 3 (see FIG. 5) having a full square section of 120×120 microns (14400 square microns), the micron ($10^{-6}$ meters) constituting the typical unit of measurement to which reference is made when determining the dimensions of the component parts of a stent.

An element of this sort may be coated by means of dipping in a substance such as a polymer, which can function as a carrier of active agents.

Tests currently carried out show that the maximum thickness of substance that can be deposited and withheld on the element 3 is in the region of 20 microns.

This means that the layer of substance facing the outside of the stent and able to perform an effective action has a sectional area of approximately 2400 square microns.

EXAMPLE 2

In an element 3 having the dimensional characteristics of the full element of Example 1, a continuous recess 4 was formed by means of laser etching according to the general geometry represented in FIG. 5. The recess had a depth (measured in the radial direction with respect to the stent) of 60 microns and a width (measured in the direction tangential to the stent) of 40 microns.

The recess thus occupied a portion corresponding to approximately 17% of the overall sectional area of the element and was able to receive inside it the same quantity of active substance as in Example 1 (sectional area corresponding to approximately 2400 square microns).

The bending moments of inertia $I_x$ and $I_y$ of the element 3 provided with the recess, determined, respectively with reference to:

An X axis oriented in a direction that is transverse and tangential with respect to the stent and a Y axis oriented in a direction that is radial with respect to the stent, were found to be equal, respectively, to 80% and 98% of the homologous moments of inertia (identical to one another, given the square section) of the element of Example 1. The moments of inertia given above are understood as being referred to centroidal axes.

EXAMPLE 3

A recess having the same sectional area as the recess of example 2 was made in an element 3, the external dimensions of which were increased to 140 microns in height (measured in the radial direction with respect to the stent) and 120 microns in width (measured in the direction orthogonal to the height), so as to have an area of metal section, and hence characteristics of resistance to longitudinal stresses, corresponding to those of the element 3 of Example 1 (14400 square microns). In this case, the recess occupied a portion corresponding to approximately 14% of the overall sectional area of the element.

The moments of inertia $I_x$ and $I_y$ determined according to the same modalities seen previously, were, respectively 116% and 112% of the homologous moments of inertia of the element of Example 1.

EXAMPLE 4

A recess having a rectangular section with a sectional area twice the sectional area of the recess of Example 2 was made in an element 3, the external dimensions of which were 160 microns in height (measured in the radial direction with respect to the stent) and 120 microns in width (measured in the direction orthogonal to the height), so as to have, also in this case, an area of metal section equal to that of the element 3 of Example 1 (14400 square microns).

In this case, the recess (depth, 80 microns; width, 60 microns) occupied a portion corresponding to approximately 25% of the overall sectional area of the element.

The moments of inertia $I_x$ and $I_y$, again determined according to the same modalities seen previously, were, respectively 160% and 125% of the homologous moments of inertia of the element of Example 1.

EXAMPLE 5

A recess having a substantially rectangular section with a sectional area of 8000 square microns, i.e., approximately 3.3 times the sectional area of the recess of Example 2, was made in an element 3, the external dimensions of which were 140 microns in height (measured in the radial direction with respect to the stent) and 160 microns in width (measured in the direction orthogonal to the height), so as to have, also in this case, an area of metal section equal to that of the element 3 of Example 1 (14400 square microns).

In this case, the recess (depth, 80 microns; width, 100 microns) occupied a portion corresponding to approximately 36% of the overall sectional area of the element.

The moments of inertia $I_x$ and $I_y$, again determined according to the same modalities seen previously, were, respectively 122% and 240% of the homologous moments of inertia of the element of Example 1.

The Examples prove the possibility of providing, at least locally, the elements 2 and 3 defining the structure of a stent with recesses 4 for receiving agents for treatment of the site of implantation of the stent. The recesses 4 occupy a substantial portion of the sectional area of the respective element while at the same time resulting in a geometry of the recesses 4 that leaves substantially unaffected the characteristics of bending strength of the respective element 2, 3, the characteristics being identified mainly by the corresponding bending moments of inertia $I_x$ and $I_y$.

The above applies in particular when the intervention is aimed at preserving the metal sectional area of the element in which the recesses are provided. The examples seen previously prove that, operating in the above way, it is indeed possible to obtain increments—even marked ones— in the aforesaid bending moments of inertia.

Of course, without prejudice to the principle of the invention, the details of construction and the embodiments may vary widely with respect to what is described and illustrated herein, without thereby departing from the scope of the present invention as defined in the annexed claims.

What is claimed is:

1. A stent for use at an implant site in a vessel comprising a radially expandable tubular body and an active agent for treatment of the implant site, the tubular body having an interior surface and an exterior surface, the tubular body including a plurality of sinusoidal shaped annular elements and a plurality of lambda shaped connection elements, each annular element being connected to at least one other annular element by a plurality of connection elements, each annular element and each connection element having a rectilinear portion and a curved portion, the exterior surface of the tubular body having a plurality of recesses positioned only in the rectilinear portions, the plurality of recesses being substantially continuous on the exterior surface of the rectilinear portions of the stent, the active agent being contained within the recesses, the recesses conferring on the rectilinear portion where they are positioned a hollowed sectional profile of which the recesses occupy from 10% to 60% of the area of the sectional profile, the geometry of the recesses being such that bending moments of inertia of the portions containing the recesses are not substantially reduced.

2. A stent for use at an implant site in a vessel comprising a radially expandable tubular body and an active agent for treatment of the implant site, the tubular body having an interior surface and an exterior surface, the tubular body including a plurality of sinusoidal shaped annular elements and a plurality of lambda shaped connection elements, each annular element being connected to at least one other annular element by a plurality of connection elements, each annular element and each connection element having a rectilinear portion and a curved portion, the exterior surface of the tubular body having a plurality of recesses positioned only in the rectilinear portions, the active agent being contained within the recesses, the recesses conferring on the rectilinear portion where they are positioned a hollowed sectional profile of which the recesses occupy from 10% to 60% of the area of the sectional profile, the geometry of the recesses being such that bending moments of inertia of the portions containing the recesses are not substantially reduced, wherein the exterior surface of the stent has a coating of biocompatible carbon material.

3. The stent of claim 2, wherein the plurality of recesses has a coating of biocompatible carbon material.

4. A stent for use at an implant site in a vessel comprising a radially expandable tubular body and an active agent for treatment of the implant site, the tubular body having an interior surface and an exterior surface, the tubular body including a plurality of annular elements and a plurality of connection elements, each annular element being connected to at least one other annular element by at least two connection elements, the tubular body having a plurality of recesses, the plurality of recesses being substantially continuous, the active agent being contained within the recesses, the recesses conferring on the elements where they are positioned a hollowed sectional profile of which the recesses occupy a portion of the area of the sectional profile, the geometry of the recesses being such that bending moments of inertia of the elements containing the recesses are not substantially reduced.

5. A stent for use at an implant site in a vessel comprising a radially expandable tubular body and an active agent for treatment of the implant site, the tubular body having an interior surface and an exterior surface, the tubular body including a plurality of sinusoidal shaped annular elements and a plurality of lambda shaped connection elements, each annular element being connected to at least one other annular element by a plurality of connection elements, each annular element and each connection element having a rectilinear portion and a curved portion, the exterior surface of the tubular body having a plurality of recesses positioned only in the rectilinear portions, the active agent being contained within the recesses, the recesses conferring on the rectilinear portion where they are positioned a hollowed sectional profile of which the recesses occupy from 10% to 60% of the area of the sectional profile, the geometry of the recesses being such that bending moments of inertia of the portions containing the recesses are not substantially reduced, wherein the exterior surface of the stent has a coating of biocompatible carbon material.

6. A stent for use at an implant site in a vessel comprising a radially expandable tubular body and an active agent for treatment of the implant site, the tubular body having an interior surface and an exterior surface, the tubular body including a plurality of sinusoidal shaped annular elements and a plurality of lambda shaped connection elements, each annular element being connected to at least one other annular element by a plurality of connection elements, each annular element and each connection element having a rectilinear portion and a curved portion, the exterior surface of the tubular body having a plurality of recesses positioned only in the rectilinear portions, the active agent being contained within the recesses, the recesses conferring on the rectilinear portion where they are positioned a hollowed sectional profile of which the recesses occupy from 10% to 60% of the area of the sectional profile, the geometry of the recesses being such that bending moments of inertia of the portions containing the recesses are not substantially reduced, wherein the plurality of recesses has a coating of biocompatible carbon material.

* * * * *